United States Patent
Manning

(10) Patent No.: US 6,468,288 B1
(45) Date of Patent: Oct. 22, 2002

(54) INSTRUMENT FOR IMPLANTING HAIR GRAFTS AND OTHER OBJECTS INTO THE EPITHELIUM OF AN ANIMAL

(76) Inventor: Allen B. Manning, 1008 Live Oak La., Arlington, TX (US) 76012

( * ) Notice: Subject to any disclaimer, the term of this patent is extended or adjusted under 35 U.S.C. 154(b) by 0 days.

(21) Appl. No.: 09/613,193

(22) Filed: Jul. 10, 2000

Related U.S. Application Data

(60) Provisional application No. 60/145,393, filed on Jul. 23, 1999.

(51) Int. Cl.$^7$ ............................................. A61B 17/34
(52) U.S. Cl. ............................ 606/187; 606/185; 63/12
(58) Field of Search ................................ 606/185, 187, 606/131–133, 184, 188, 117; 63/12–13; 119/866

(56) References Cited

U.S. PATENT DOCUMENTS

| | | | | |
|---|---|---|---|---|
| 149,219 A | * | 3/1874 | Hart ............................. | 119/866 |
| 2,713,863 A | * | 7/1955 | Handerson ............... | 134/169 R |
| 3,608,095 A | | 9/1971 | Barry | |
| 3,858,245 A | | 1/1975 | Nate, II et al. | |
| 4,050,100 A | | 9/1977 | Barry | |
| 4,346,713 A | | 8/1982 | Malmin | |
| 4,382,444 A | | 5/1983 | Malmin | |
| 4,583,540 A | * | 4/1986 | Malmin ....................... | 128/330 |
| 5,234,438 A | * | 8/1993 | Semrad ....................... | 606/108 |
| 5,382,257 A | * | 1/1995 | Lewis et al. ................. | 606/148 |
| 5,665,093 A | * | 9/1997 | Atkins et al. .................. | 606/1 |
| 5,782,851 A | | 7/1998 | Rassman | |
| 5,888,202 A | | 3/1999 | Amiri | |
| 6,059,807 A | * | 5/2000 | Boudejma ................... | 606/187 |
| 6,105,392 A | * | 8/2000 | Biagi ............................ | 63/12 |
| 6,167,725 B1 | * | 1/2001 | Sierkierski ................... | 63/12 |

* cited by examiner

Primary Examiner—Kennedy Schaetzle
Assistant Examiner—Kristen Droesch
(74) Attorney, Agent, or Firm—Merchant & Gould, LLC

(57) ABSTRACT

An implantation device is disclosed. The implantation device includes a curved main shaft having a first end and a second end, and a removable penetrating tip fitted onto the second end of the main shaft. The implantation device may be used to implant any object, particularly hair follicles, into the epithelium and/or subcutaneous tissue of a patient. A method of implanting an object into the epithelium and/or subcutaneous tissue of a patient is also disclosed.

49 Claims, 4 Drawing Sheets

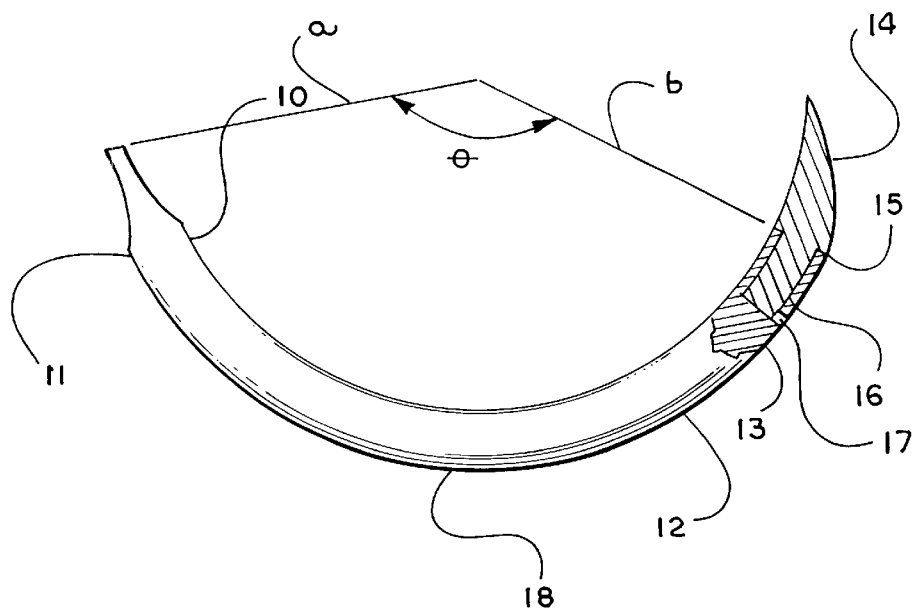
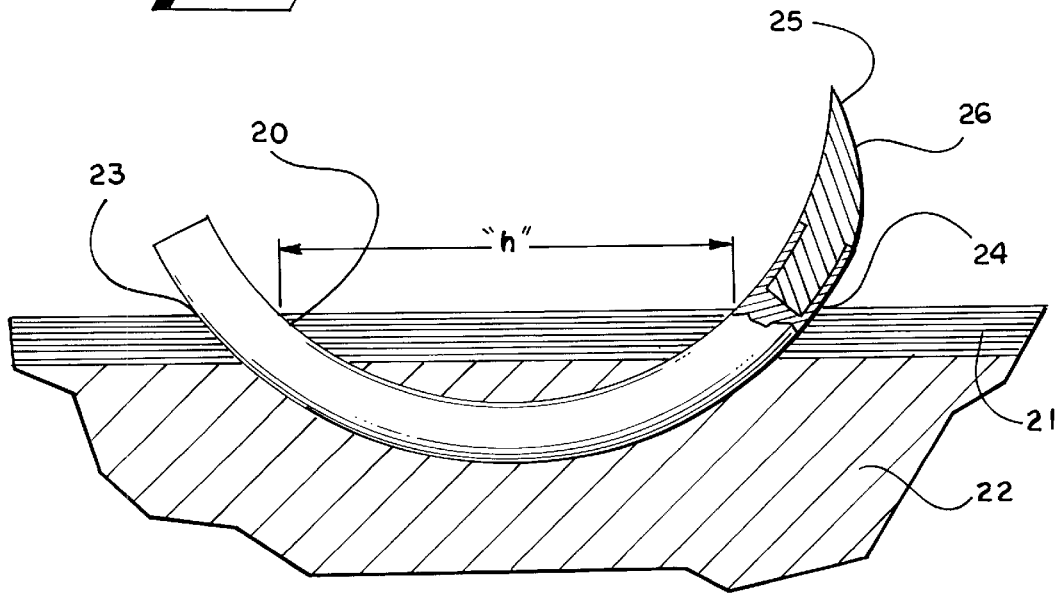

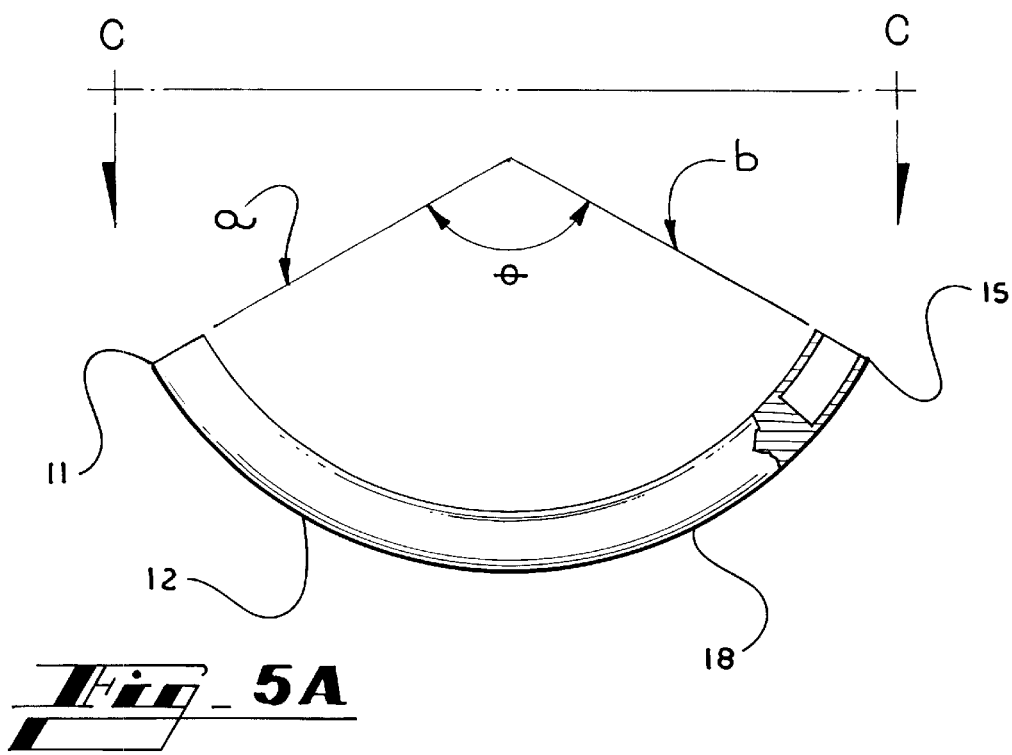
Fig_5A
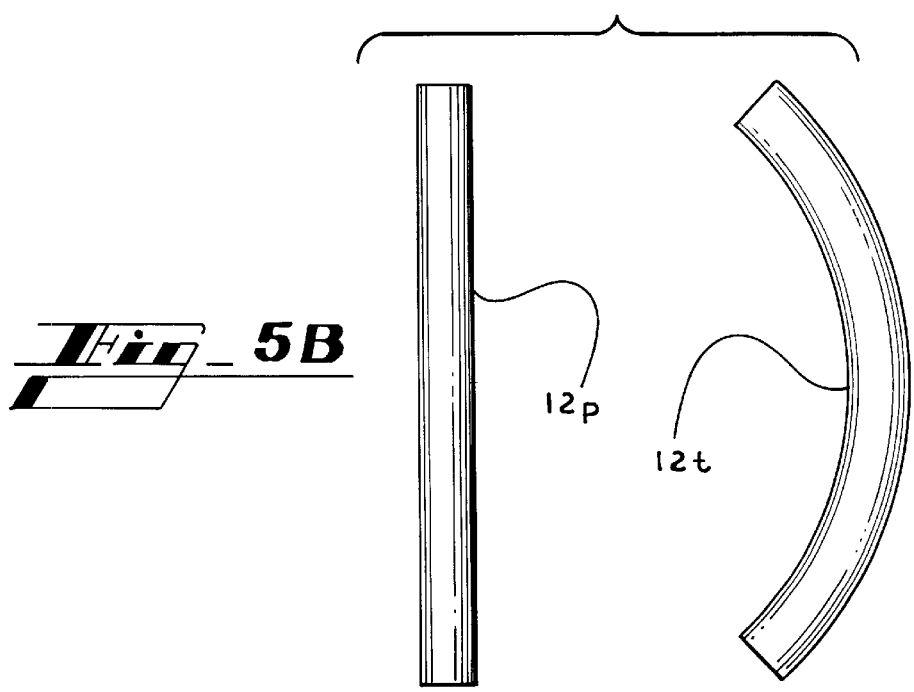
Fig_5B

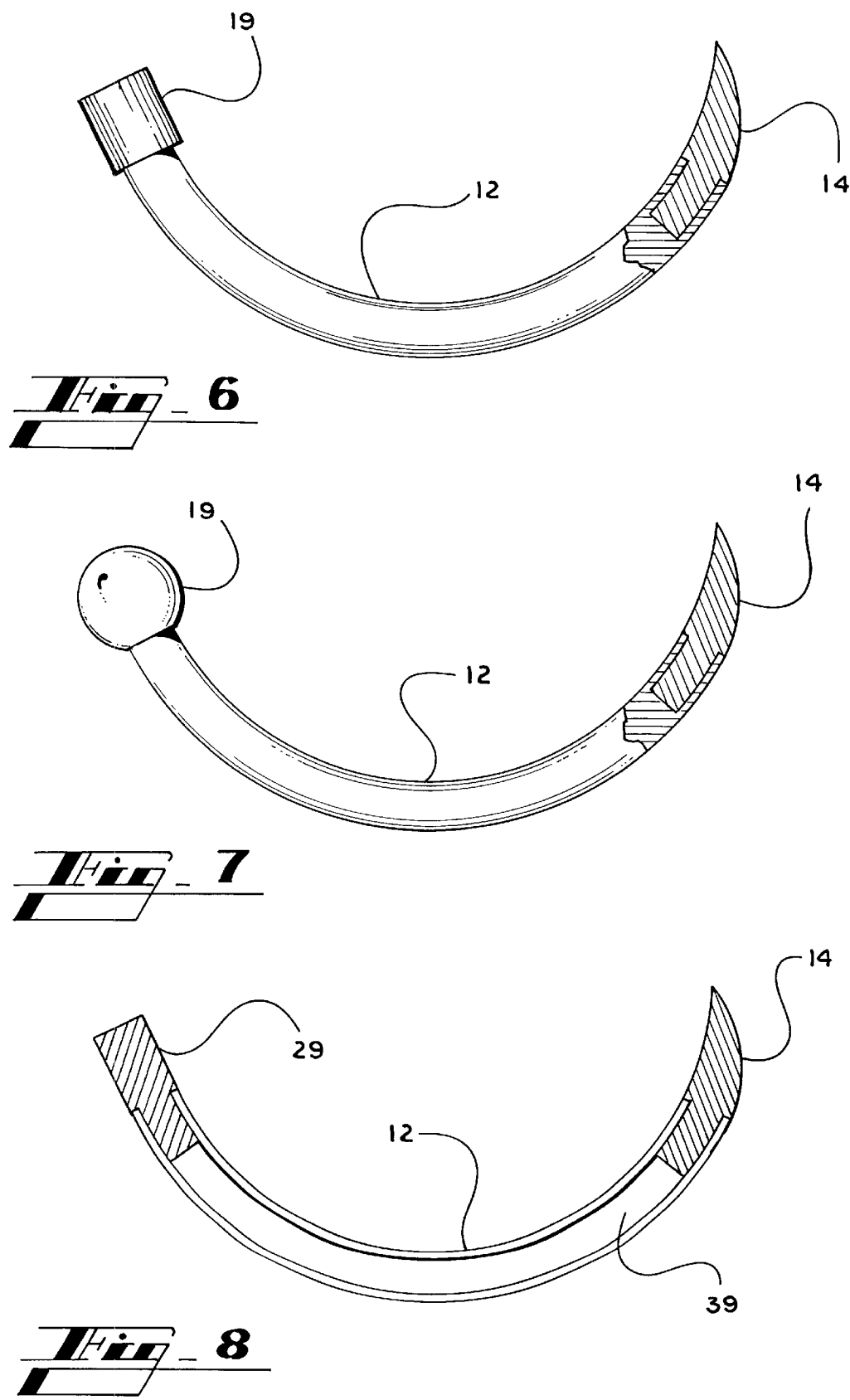

ial for implanting hair

INSTRUMENT FOR IMPLANTING HAIR GRAFTS AND OTHER OBJECTS INTO THE EPITHELIUM OF AN ANIMAL

CROSS-REFERENCE TO RELATED APPLICATIONS

This patent application claims the benefit of priority to U.S. provisional patent application 60/145,393, filed on Jul. 23, 1999.

FIELD OF THE INVENTION

The present invention is directed to an instrument for implanting an object into the epithelium and/or subcutaneous tissue of an animal, particularly hair grafts. The present invention is further directed to a method of implanting an object into the epithelium and/or subcutaneous tissue of an animal.

BACKGROUND OF THE INVENTION

In recent years, a significant industry has developed which involves the implantation of naturally-growing hair from one or more hair-bearing areas of a patient's body to one or more hair-deficient areas of the body. Historically, hair implantation techniques have evolved from larger plug-graphs, containing up to about 35 hair follicles, to smaller micro- or mini-grafts. The plug-grafts resulted in scattered patches of hair growth (i.e., the "corn row effect"), as opposed to a natural-looking, hair-bearing scalp. The smaller micro- or mini-grafts, having less than about 6 hair follicles, have become the current methods of choice due to the resulting cosmetic effect, resembling natural hair.

Much effort has been directed at generally improving the process of implanting hair follicles into a hair-deficient area of the scalp or other area. As disclosed in U.S. Pat. Nos. 5,584,841 and 5,782,851 issued to Rassman, various instruments for implanting hair are known to those of ordinary skill in the art. While the known instruments result in the implantation of hair follicles, the instruments may cause undesired trauma to hair grafts and the scalp during the implantation procedure. Further, the known instruments do not provide an adequate amount of control over the positioning of the hair graft once implanted.

What is needed in the art is an instrument for implanting a hair graft or other object into the epithelium and/or subcutaneous tissue of an animal without traumatizing the hair graft during the implantation procedure. What is also needed in the art is a method of implanting a hair graft or other object into the epithelium and/or subcutaneous tissue of an animal wherein the surgeon has complete control over the position of the hair graft or other object during the implantation procedure.

SUMMARY OF THE INVENTION

The present invention addresses some of the difficulties and problems discussed above by the discovery of an implantation device, which minimizes the amount of trauma on an object, such as a hair follicle, during an implantation procedure. The implantation device further provides enhanced control over the positioning of the object within the patient's epithelium and/or subcutaneous tissue. The implantation device may be used to implant a variety of objects within a patient's epithelium and/or subcutaneous tissue, and has particular use in the area of hair implantation.

The present invention is also directed to a method of implanting an object, such as a hair follicle, into the epithelium and/or subcutaneous tissue of a patient. The method includes the steps of inserting the implantation device into a first area of the body; causing a leading end of the implantation device to exit a second area of the body; removing the tip of the device to expose a hollow cavity of the device; inserting an object to be implanted, such as a hair follicle, into the hollow cavity of the device; and surgically positioning the object by withdrawing the device while grasping an end portion of the implanted object, controlling the level of implantation of the object as the device is removed from the epithelium and/or subcutaneous tissue of a patient.

These and other features and advantages of the present invention will become apparent after a review of the following detailed description of the disclosed embodiments and the appended claims.

BRIEF DESCRIPTION OF THE DRAWINGS

FIG. 1 depicts an implantation device of the present invention.

FIG. 2 depicts an implantation device of the present invention inserted in a patient's body such that a leading end of the implantation device protrudes from the body.

FIG. 5a depicts a main shaft of an implantation device of the present invention and how the angle of curvature is measured.

FIG. 5b depicts two main shafts of implantation devices of the present invention illustrating a planar configuration and a three-dimensional configuration when viewing a main shaft in a plane, such as along line C—C of FIG. 5a.

FIG. 6 depicts an implantation device of the present invention having an attachment on an end of the main shaft opposite to the removable tip.

FIG. 7 depicts an implantation device of the present invention having a decorative object on an end of the main shaft opposite to the removable tip.

FIG. 8 depicts an implantation device of the present invention having a second removable portion on an end of the main shaft opposite to the removalbe tip.

DETAILED DESCRIPTION OF THE INVENTION

Figure 3:
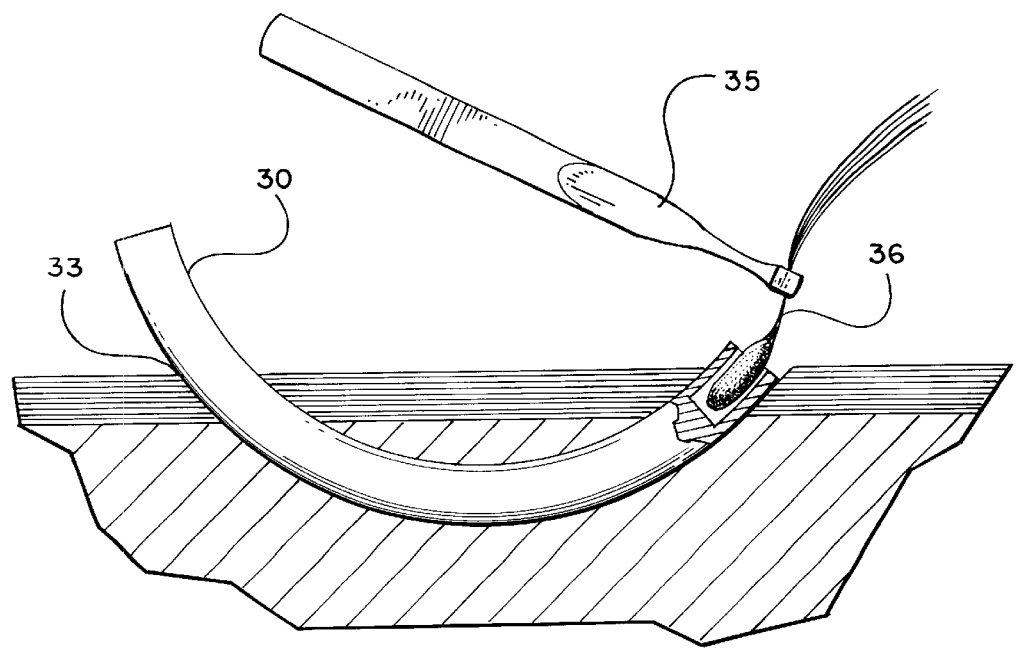
FIG. 3 depicts an implantation device of the present invention, containing an object to be implanted, being surgically manipulated to a desired level of implantation.

The present invention is directed to an implantation device for inserting an object into the epithelium and/or subcutaneous tissue of an animal. In one embodiment of the present invention, the implantation device is used to insert a hair graft into the skin. In a further embodiment, the device is used to insert a body-piercing, decorative material, such as a string or wire, through the epithelium and/or subcutaneous tissue of an animal. The implantation device enables the implantation of an object into the epithelium and/or subcutaneous tissue, while mining the amount of damage to the object to be implanted.

The implantation device of the present invention may have a variety of shapes and sizes. One example of the implantation device of the present invention is shown in FIG. 1. The implantation device 10 comprises two components: a main shaft 12 and a removable tip 14. Main shaft 12 comprises a first end 11 and a second end 13, separated and connected by a curved section 18. Removable tip 14 fits snugly into main shaft 12 at an opening 15 in second end 13 of the implantation device. A portion of removable tip 14 fills a hollow cavity 16 within main shaft 12 at second end 13. A small opening 17 may be present in main shaft 12 in order to provide a connection between an interior end of hollow cavity 16 and an outer surface of main shaft 12.

The implantation device 10 may have an overall length, which may vary depending on a number of factors including, but not limited to, its intended use. Typically, the implantation device has an overall length of less than about 10 cm. Desirably, the overall length of the implantation device is from about 2 cm to about 8 cm. More desirably, the overall length of the implantation device is from about 3 cm to about 6 cm. Each section of the main shaft of the implantation device (i.e., first end 11, curved section 18, and second end 13) may also have a variety of lengths. Further, the angle of curvature in curved section 18 may also vary as desired. As used herein, the phrase "angle of curvature" is used to describe the amount of curvature, in degrees, between first end 11 and second end 13. Desirably, the angle of curvature is from about 120° to about 210°. More desirably, the angle of curvature is from about 160° to about 200°. Even more desirably, the angle of curvature is from about 170° to about 190°.

The angle of curvature in curved section 18 may be measured as shown in FIG. 5*a*. Angle of curvature, θ, is the angle formed between lines a and b, which are perpendicular to main shaft 12 at ends 11 and 15 respectively. As discussed above, angle of curvature, θ, is desirably from about 120° to about 210°, so in one exemplary embodiment, the main shaft of the implantation device resembles a semi-circle (i.e., angle of curvature, θ, is equal to 120°).

The implantation device of the present invention may have a planar configuration or may have a three-dimensional configuration. As used herein, the term "planar configuration" is used to describe an implantation device of the present invention, which lies substantially flat when placed on a planar surface, such as a tabletop. As used herein, the term "three-dimensional configuration" is used to describe an implantation device of the present invention, which does not lay substantially flat when placed on a planar surface. An example of an implantation device of the present invention, which has a three-dimensional configuration, is an implantation device having a corkscrew-type configuration, which also has the above-described angle of curvature. A further example of an implantation device of the present invention, which has a three-dimensional configuration, is an implantation device having a coil-type configuration, which also has the above-described angle of curvature. Such implantation devices may have any number of turns or any fraction of a turn along the length of the implantation device. As used herein, the term "turn" is used to describe the number of spirals or circles along the length of an implantation device, which has a three-dimensional configuration.

FIG. 5*b* depicts two exemplary main shafts of implantation devices of the present invention, one having a planar configuration and the other having a three-dimensional configuration. When viewing a main shaft along a plane, such as along line C—C of FIG. 5*a*, the main shaft of the implantation device may have a planar configuration, such as main shaft 12*p*, or a three-dimensional configuration, such as main shaft 12*t*, as shown in FIG. 5*b*.

The implantation device of the present invention may have a diameter, circumference and cross-sectional shape, which varies depending on a number of factors including, but not limited to, the size of the object to be implanted. As used herein, the term "diameter" refers to the maximum cross-sectional dimension of the main shaft or removable tip. The diameter, circumference and cross-sectional shape of the implantation device may vary along the length of main shaft 12, but typically the diameter, circumference and cross-sectional shape remain substantially the same along the length of main shaft 12 of the device. Desirably, the main shaft 12 has a circular cross-sectional shape, a diameter of less than about 4 mm, and a circumference of less than about 12 mm. More desirably, the main shaft 12 has a circular cross-sectional shape, a diameter of from about 1 mm to about 3 mm, and a circumference of from about 3 mm to about 9 mm.

It should be noted that the cross-sectional shape of main shaft 12 may have a variety of shapes including, but not limited to, circular, square, octagonal, rectangular, oval, etc. It should further be noted that the cross-sectional shape of implantation device 10 of the present invention may vary along the length of the main shaft 12 and removable tip 14. In one embodiment of the present invention, the cross-sectional shape near the point of removable tip 14 is circular, and gradually changes to a square, octagonal, rectangular or oval cross-sectional shape along a section of removable tip 14 or main shaft 12.

The implantation device of the present invention further includes a hollow cavity 16 in the second end 13 of main shaft 12. Desirably, the cross-sectional area of hollow cavity 16 is maximized in order to provide space for an object to be implanted. The depth of the hollow cavity may vary, but typically the depth of hollow cavity is less than about 20 mm. Desirably, the depth of hollow cavity 16 is from about 3 mm to about 12 mm in length. More desirably, the depth of hollow cavity 16 is from about 4 mm to about 8 mm in length. Hollow cavity 16 may also have an opening 17 positioned at an interior end of hollow cavity 16, which allows for fluid flow between an interior portion of hollow cavity 16 and the outer surface of main shaft 12. Opening 17 may have a variety of dimensions and shapes, but typically opening 17 is circular or oval and has a diameter of less than about 1 mm.

The implantation device of the present invention further comprises a removable tip 14, a first end of which may be fitted into hollow cavity 16 of main shaft 12. A second end of removable tip 14, opposite to the first end, forms a sharp point or edge, which is capable of surgically penetrating the epithelium and/or subcutaneous tissue of a patient. The outer surface of the removable tip 14 forms a smooth connection to main shaft 12 at opening 15 of the implantation device. In one embodiment of the present invention, removable tip 14 has an angle of curvature slightly smaller or larger than the angle of curvature of main shaft 12. The difference in the angle of curvatures creates a mechanical spring mechanism, which contributes to the mechanical friction between the removable tip and the main shaft, further enhancing the connection between the removable tip and the main shaft. Although unnecessary, other means may be used to enhance the connection between the removable tip and the main shaft if desired including, but not limited to, a mechanical locking device or an adhesive. Other alternative means may be used to connect removable tip 14 to main shaft 12. Such alternative means include, but are not limited to, matching threads such that removable tip 14 may be screwed into and out of main shaft 12.

The implantation device of the present invention may be made from a variety of materials. Suitable materials include any material capable of being formed into main shaft 12 and removable tip 14, and having sufficient strength and rigidity to be inserted through the epithelium and subcutaneous tissue of a patient. Suitable materials include, but are not limited to, metals, plastics, and ceramics. Desirably, both main shaft 12 and removable tip 14 are formed from metallic materials, such as stainless steel.

In one embodiment of the present invention, a portion of main shaft 12 of the implantation device at first end 11 is flattened. Such an exemplary embodiment is shown in FIG. 1. In this embodiment, the flattened end of the implantation device may be grasped by an instrument, such as a flat-jawed needle holder instrument (i.e., needle-nose pliers).

In a further embodiment of the present invention, the implantation device comprises an attachment 19 on the end of main shaft 12 opposite removable tip 14. Such an exemplary implantation device of the present invention is shown in FIG. 6. The attachment 19 may be used to provide a better grasp of the implantation device. The attachment 19 may be as simple as a temporary rubber sleeve or more complex, such as a molded plastic part, which allows easy manipulation and/or grasping of the device by a user's fingers. In a further embodiment of the present invention, the implantation device may be permanently attached to an attachment 19, such as a molded plastic or metallic handle, to form a hand-held surgical instrument.

Main shaft 12 and/or removable tip 14 of the implantation device may be reusable and surgically sterilizable. Alternatively, main shaft 12 and/or removable tip 14 of the implantation device may be disposable. In one embodiment of the present invention, the implantation device is reusable and packaged in a surgically sterilized container. In a further embodiment of the present invention, the implantation device is disposable and packaged in a surgically sterilized container.

The present invention is further directed to a method of implanting an object into the epithelium and/or subcutaneous tissue of a patient. Although the implantation device finds particular utility in the area of hair graft implantation, the implantation device may be used to implant other objects into the epithelium and/or subcutaneous tissue of a patient. Suitable objects include, but are not limited to, string, metal, loops, wire, synthetic or naturally-occurring yarns, and other body-piercing objects. The method of the present invention enables the implantation of an object (1) without traumatizing the object being implanted, (2) with precise control over the position of the object to be implanted, and (3) while minimizing the amount of trauma to the epithelium and/or subcutaneous tissue of the patient.

The implantation method of the present invention includes the steps of inserting the implantation device into a first area of an animal's body so that a leading end of the implantation device exits out of a second area of the animal's body; removing the tip of the device to expose a hollow cavity of the device; inserting an object to be implanted, such as a hair graft or follicle, into the hollow cavity of the device; and surgically positioning the object by withdrawing the device while grasping an end portion of the implanted object, controlling the level of implantation of the object as the device is removed from the epithelium and/or subcutaneous tissue of a patient. Typically, the distance "h" between the first area of the body and the second area of the body is less than about 40 mm. More desirably, the distance "h" between the first area of the body and the second area of the body is from about 5 mm to about 30 mm. Even more desirably, the distance "h" between the first area of the body and the second area of the body is from about 10 mm to about 20 mm.

FIG. 2 of the drawings depicts an implantation device 20 of the present invention when inserted through a patient's skin 21 and subcutaneous tissue 22. The implantation device 20 enters the skin 21 at first area 23 and exits skin 21 at second area 24, a distance "h" from first area 23. Once the leading end 25 of the implantation device exits the skin 21, removable tip 26 of the implantation device may be removed to expose the hollow cavity of the implantation device. An object, such as a hair graft, may then be inserted into the hollow cavity, manually by hand or with the aid of a separate tool. In one embodiment of the present invention, a suction device is used to pull an object into the hollow cavity. In this embodiment, the suction device may be positioned over opening 17 (shown in FIG. 1) to aid in the insertion of an object into the hollow cavity.

Once an object is inserted into the hollow cavity of the implantation device, the object is surgically positioned by withdrawing the device while grasping an end portion of the object to be implanted, controlling the level of implantation of the object as the device is removed from the epithelium and/or subcutaneous tissue of a patient. As shown in FIG. 3, implantation device 30 exits a patient's body at first area 33. A set of tweezers 35 may be used to surgically position object 36 in place, while implantation device 30 is removed from the epithelium and/or subcutaneous tissue of the patient. It should be understood that any device may be used to surgically position the object, while the implantation device is removed from the patient's body. Suitable positioning devices include, but are not limited to, tweezers, fingers, or any other clasping device.

Figure 4:
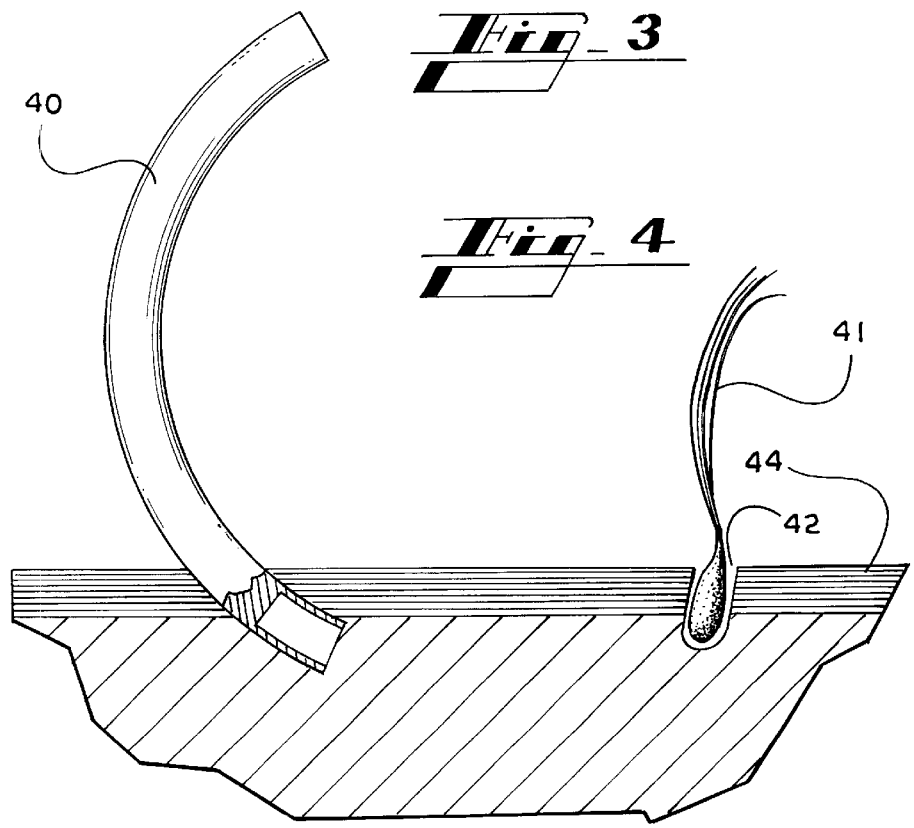
FIG. 4 depicts an object implanted in a patient's body after being implanted by and detached from an implantation device of the present invention.

FIG. 4 displays an object 41 implanted in a patient's body 42 after being implanted by and detached from implantation device 40 of the present invention. As the main shaft of implantation device 40 is surgically manipulated in a retrograde fashion, object 41 is positioned at a desired level within patient body 42. The angle of placement relative to the skin surface 44 determines the direction of object 41 protruding from the skin surface 44. In an embodiment of the present invention wherein the object is a hair graft, the operator of the implantation device may manipulate the exit-thrust through the epithelium and subcutaneous tissue via surgical technique to obtain a desired angle of implantation and angle of hair growth.

In a further embodiment of the present invention, the object to be implanted may be pushed into and through the patient's body along the pathway of the implantation device as the device is removed from the patient's body. Objects such as metal loops or rings may be inserted into the body of an animal in this manner.

In yet a further embodiment of the present invention, the object to be implanted into a patient's body may be the implantation device itself. In this embodiment, the removable tip may be removed and replaced by a replacement tip. A variety of replacement tips may be connected to the main shaft of the implantation device by any attachment means described above including, but not limited to, varying the angle of curvature of the main shaft and the replacement tip, screwing the replacement tip on the main shaft, and adhesives. Suitable replacement tips include any object that has been designed to be attached to the main shaft of the implantation device. Suitable replacement tips include, but are not limited to, decorative tips, such as metal balls, "skull and crossbones," jewel-containing tips, or metal tips; and informational tips, such as one's initials, fraternity symbol, or any other type of symbol. It should be noted that an object, which is identical to or different from the replacement tip, may be temporarily or permanently connected to the main shaft opposite to the replacement tip to produce a symmetrical or unsymmetrical effect when the implantation device is the object to be implanted into a patient's body.

FIG. 7 depicts an exemplary implantation devices of the present invention having a main shaft 12, a removable tip 14, and a decorative object 79 as described above. In FIG. 7, the decorative object 79 is shown as a metal ball, however, decorative object 79 may be any object as described above.

The implantation device of the present invention may further comprise a second removable portion, opposite to the removable tip. Such an exemplary implantation device of the present invention is shown in FIG. 8. The second removable portion 29 may be temporarily attached to the main shaft 12 of the implantation device by attachment means as described above in relation to the removable tip 14. In this embodiment, a second object, which is identical to or different from the replacement tip, may be temporarily or permanently connected to the main shaft opposite to the replacement tip to produce a symmetrical or unsymmetrical effect when the implantation device is the object to be implanted into a patient's body.

In addition to a second removable portion 29, the implantation device of the present invention may further comprise a hollow shaft 39, which runs the entire length of the main shaft 12. Such an exemplary implantation device of the present invention is also shown in FIG. 8. Further decorative effects may be achieved in this embodiment by removing both ends of the implanted implantation device and inserting a string or wire through the main shaft. The string or wire may then be used to suspend objects from the patient's body. Alternatively, two hollow replacement tips may be attached to both ends of the main shaft prior to threading a string or wire through the implanted implantation device. Such replacement tips may be shaped so as to limit the movement of the implanted implantation device, i.e., to prevent either end of the implanted implantation device from entering the epithelium and/or subcutaneous tissue of the patient's body.

The present invention is further described by the example which follows. Such an example, however, is not to be construed as limiting in any way either the spirit or scope of the present invention.

EXAMPLE

Implantation of Hair Grafts

An implantation device was prepared from stainless steel and surgically sterilized. The implantation device had an overall length of 4 cm, a circular cross-section, and a diameter of 2 mm along the length of the device. The implantation device had a removable tip at one end and a flattened end, opposite the removable tip. The removable tip had an angle of curvature slightly smaller than the angle of curvature of the main shaft of the implantation device.

Hair grafts containing from one to about 4 hair follicles were dissected from an excised portion of a hair-bearing area of a patient's scalp. The hair grafts were implanted into a hair-deficient area of the patient's scalp using the above-described implantation device.

While the specification has been described in detail with respect to specific embodiments thereof, it will be appreciated that those skilled in the art, upon attaining an understanding of the foregoing, may readily conceive of alterations to, variations of, and equivalents to these embodiments. For example, other uses may be suitable for the implantation device of the present invention, such as implanting a foreign object into an inanimate object. Accordingly, the scope of the present invention should be assessed as that of the appended claims and any equivalents thereto.

What is claimed is:

1. An implantation device comprising, an arcuate main shaft having a first end and a second end, wherein the second end contains a hollow cavity, and the main shaft has an angle of curvature of from about 120° to about 210°;

a removable tip having a first portion and a second portion, wherein the first portion of the removable tip fits into the hollow cavity of the main shaft and the second portion forms a point or edge capable of penetrating the epithelium and subcutaneous tissue of an animal; and a second removable portion attached to the main shaft opposite to the removable tip.

2. The implantation device of claim 1, wherein the main shaft is hollow along an entire length of the main shaft.

3. The implantation device of claim 1, wherein the main shaft has a diameter of from about 1 mm to about 3 mm, a circular cross-sectional shape, and a circumference of from about 3 mm to about 9 mm.

4. The implantation device of claim 1, wherein the second removable portion consists of a metal ball, a skull and crossbones, a jewel-containing object, a metal object, one or more initials, a fraternity symbol, or a tip for preventing an end of the main shaft from entering the epithelium of an animal.

5. The implantation device of claim 1, wherein the second removable portion and the hollow cavity of the main shaft opposite the removable tip both contain threads such that the second removable portion screws into the main shaft.

6. The implantation device of claim 1 wherein the second portion of the removable tip forms a point.

7. An implantation device comprising:

an arcuate main shaft having a first end and a second end, wherein the second end contains a hollow cavity, and the shaft has an angle of curvature of from about 120° to about 210°;

a removable tip having a first portion and a second portion, wherein the first portion of the removable tip fits into the hollow cavity of the main shaft and the second portion forms a point or edge capable of penetrating the epithelium and subcutaneous tissue of all animal; and an attachment on an end of the main shaft opposite to the removable tip; wherein the attachment consists of a temporary rubber sleeve, a molded plastic part, or a metallic handle.

8. The implantation device of claim 7, wherein the main shaft has a diameter of from about 1 mm to about 3 mm, a circular cross-sectional shape, and a circumference of from about 3 mm to about 9 mm.

9. The implantation device of claim 7, wherein the second portion of the removable tip forms a point.

10. An implantation device comprising;

an arcuate main shaft having a first end and a second end, wherein the second end contains a hollow cavity, and the main shaft has an opening between an interior end of the hollow cavity and an outer surface of the main shaft;

a removable tip having a first portion and a second portion, wherein the first portion of the removable tip fits into the hollow cavity of the main shaft and the second portion forms a point or edge capable of penetrating the epithelium and subcutaneous tissue of an animal; and an attachment on an end of the main shaft opposite to the removable tip; wherein the attachment consists of a temporary rubber sleeve, a molded plastic part, or a metallic handle.

11. The implantation device of claim 10, wherein the second portion of the removable tip forms a point.

12. An implantation device consisting of:
   a single arcuate main shaft having a first end and a second end, wherein the second end contains a hollow cavity; and
   a removable tip having a first portion and a second portion, wherein the first portion of the removable tip fits into the hollow cavity of the main shaft and the second portion forms a point or edge capable of penetrating the epithelium and subcutaneous tissue of an animal.

13. The implantation device of claim 12, wherein the main shaft has a first outer surface at the second end of the main shaft; the removable tip has a second outer surface along the removable tip between the first portion and the second portion of the removable tip; and wherein the first outer surface of the main shaft and the second outer surface of the removable tip form a smooth connection between the main shaft and the removable tip.

14. The implantation device of claim 12, wherein the main shaft has an angle of curvature of from about 120° to about 210°.

15. The implantation device of claim 14, wherein the main shaft has an angle of curvature of from about 170° to about 190°.

16. The implantation device of claim 12, wherein the main shaft has an opening between an interior end of the hollow cavity and an outer surface of the main shaft.

17. The implantation device of claim 12, wherein the removable tip has an angle of curvature different from the angle of curvature of the main shaft.

18. The implantation device of claim 12, wherein the removable tip may be screwed into the hollow cavity of the main shaft.

19. The implantation device of claim 12, wherein the main shaft has a diameter of less than about 4 mm.

20. The implantation device of claim 19, wherein the main shaft has a diameter of from about 1 mm to about 3 mm.

21. The implantation device of claim 12, wherein the implantation device has an overall length of less than about 10 cm.

22. The implantation device of claim 21, wherein the implantation device has an overall length of from about 2 cm to about 8 cm.

23. The implantation device of claim 22, wherein the implantation device has an overall length of from about 3 cm to about 6 cm.

24. The implantation device of claim 12, wherein a portion of the first end of the main shaft is flattened.

25. The implantation device of claim 12, wherein the main shaft has a circular cross-sectional shape, and a circumference of less than about 12 mm.

26. The implantation device of claim 12, wherein the main shaft has an angle of curvature of from about 120° to about 210°, a diameter of from about 1 mm to about 3 mm, a circular cross-sectional shape, and a circumference of from about 3 mm to about 9 mm; and The implantation device has an overall length of from about 3 cm to about 6 cm.

27. The implantation device of claim 12, wherein the implantation device has a three-dimensional configuration such that the implantation device does not lay flat when placed on a planar surface.

28. The implantation device of claim 12, wherein the hallow cavity has a depth o f less than 20 mm.

29. The implantation device of claim 28, wherein the hollow cavity has a depth of from about 3 mm to about 12 mm.

30. The implantation device of claim 29, wherein the hollow cavity has a depth of from about 4 mm to about 8 mm.

31. The implantation device of claim 12, wherein the main shaft and the removable tip each independently consist of a metal, plastic, or ceramic material.

32. The implantation device of claim 31, wherein the main shaft and the removable tip comprise stainless steel.

33. The implantation device of claim 12, wherein the second portion of the removable tip forms a point.

34. An implantation device consisting of:
   a single arcuate main shaft having a first end and a second end, wherein the second end contains a hollow cavity;
   a removable tip having a first portion and a second portion, wherein the first portion of the removable tip fits into the hollow cavity of the main shaft and the second portion forms a point or edge capable of penetrating the epithelium and subcutaneous tissue of an animal; and
   a decorative object attached to the main shaft opposite to the removable tip;
   wherein the main shaft has a first outer surface at the second end of the main shaft; the removable tip has a second outer surface along the removable tip between the first portion and the second portion of the removable tip; and wherein the first outer surface of the main shaft and the second outer surface of the removable tip form a smooth connection between the main shaft and the removable tip; and wherein the main shaft has an angle of curvature of from about 120° to about 210°.

35. The implantation device of claim 34, wherein the decorative object comprises a metal ball, a skill and crossbones, a jewel-containing object, a metal object, one or more initials, a fraternity symbol, or a tip for preventing an end of the main shaft from entering the epithelium of an animal.

36. The implantation device of claim 34, wherein the second portion of the removable tip forms a point.

37. An implantation device for implanting a hair graft or object into the epithelium and subcutaneous tissue of an animal, wherein the device comprises:
   a single arcuate main shaft having a first end and a second end, wherein the second end contains a hollow cavity; and
   a removable tip having a first portion and a second portion, wherein the first portion of the removable tip fits into the hollow cavity of the main shaft and the second portion forms a point or edge capable of penetrating the epithelium and subcutaneous tissue of an animal;
   wherein the main shaft has a first outer surface at the second end of the main shaft; the removable tip has a second outer surface along the removable tip between the first portion and the second portion of the removable tip; and wherein the first outer surface of the main shaft and the second outer surface of the removable tip form a smooth connection between the main shaft and the removable tip; and wherein the main shaft has an angle of curvature of from about 120° to about 210°, a diameter of from about 1 mm to about 3 mm, a circular cross-sectional shape, and a circumference of from about 3 mm to about 9 mm; and the implantation device has an overall length of from about 3 cm to about 6 cm.

38. The implantation device of claim 37, wherein the second portion of the removable tip forms a point.

39. A method of implanting an object into an animal, the method comprising:

inserting an implantation device into a first area of the animal so that a leading end of the implantation device exits a second area of the animal;

removing a portion of the implantation device to expose a hollow cavity within the implantation device;

inserting an object into the hollow cavity; and positioning the object within the animal while removing the device from the animal.

40. The method of claim 39, wherein the implantation device comprises:

a main shaft having a first end and a second end, wherein the second end contains the hollow cavity; and a removable tip having a first portion and a second portion, wherein the first portion of the removable tip fits into the hollow cavity of the main shaft and the second portion forms a point or edge capable of penetrating the epithelium and subcutaneous tissue of an animal.

41. The method of claim 39, wherein the object comprises a hair graft or a body-piercing object.

42. The method of claim 39, wherein the object comprises a hair graft.

43. The method of claim 39, further comprising grasping an end portion of the object for controlling the position of the object.

44. The method of claim 39, further comprising guiding the object into the second area along with the implantation device through the first area.

45. A method of implanting a hair graft into a patient comprising:

inserting an implantation device into a first area of the patient so that a leading end of the implantation device exits a second area of the patient;

removing a portion of the implantation device to expose a hollow cavity within the implantation device;

inserting a hair graft into the hollow cavity; and removing the implantation device from the patient while controlling the position of the hair graft.

46. The method of claim 45, wherein the implantation device comprises:

a main shaft having a first end and a second end, wherein the second end contains the hollow cavity; and a removable tip having a first portion and a second portion, wherein the first portion of the removable tip fits into the hollow cavity of the main shaft and the second portion forms a point or edge capable of forming an incision in a portion of a human body.

47. The method of claim 45, further comprising grasping an end portion of the hair graft for controlling the position of the hair graft.

48. The method of claim 45, wherein the hair graft contains up to about 35 hair follicles.

49. The method of claim 45, wherein the hair graft contains up to about 6 hair follicles.

* * * * *